United States Patent
Dawson

(10) Patent No.: US 6,323,198 B1
(45) Date of Patent: Nov. 27, 2001

(54) PREPARATION AND USE OF A SPECIFIC GABA-$_A\alpha_5$ RECEPTOR LIGAND FOR TREATMENT OF ALZHEIMER'S DISEASE

(75) Inventor: Gerard Raphael Dawson, Arkesden (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 17 days.

(21) Appl. No.: 09/621,319

(22) Filed: Jul. 20, 2000

Related U.S. Application Data (6262) Division of application No. 08/894,031, filed as application No. PCT/GB96/00377 on Feb. 20, 1996.

(30) Foreign Application Priority Data

Feb. 23, 1995 (GB) .................................. 9503601

(51) Int. Cl.$^7$ ...................................... A61K 31/55
(52) U.S. Cl. ............................... 514/220; 514/221
(58) Field of Search ........................... 514/211.09, 211.1, 514/211.12, 221, 220

(56) References Cited

PUBLICATIONS

R. Liu et al., Med. Chem. Res. vol. 5, pp 700–709, 1995.*

* cited by examiner

Primary Examiner—Zohreh Fay
(74) Attorney, Agent, or Firm—Shuy Muk Lee; David L. Rose

(57) ABSTRACT

A method of treatment for enhancing cognition in the treatment of Alzheimer's disease, for example, employs a specific GABA$_A$ Alpha5 receptor ligand.

Figure 1:
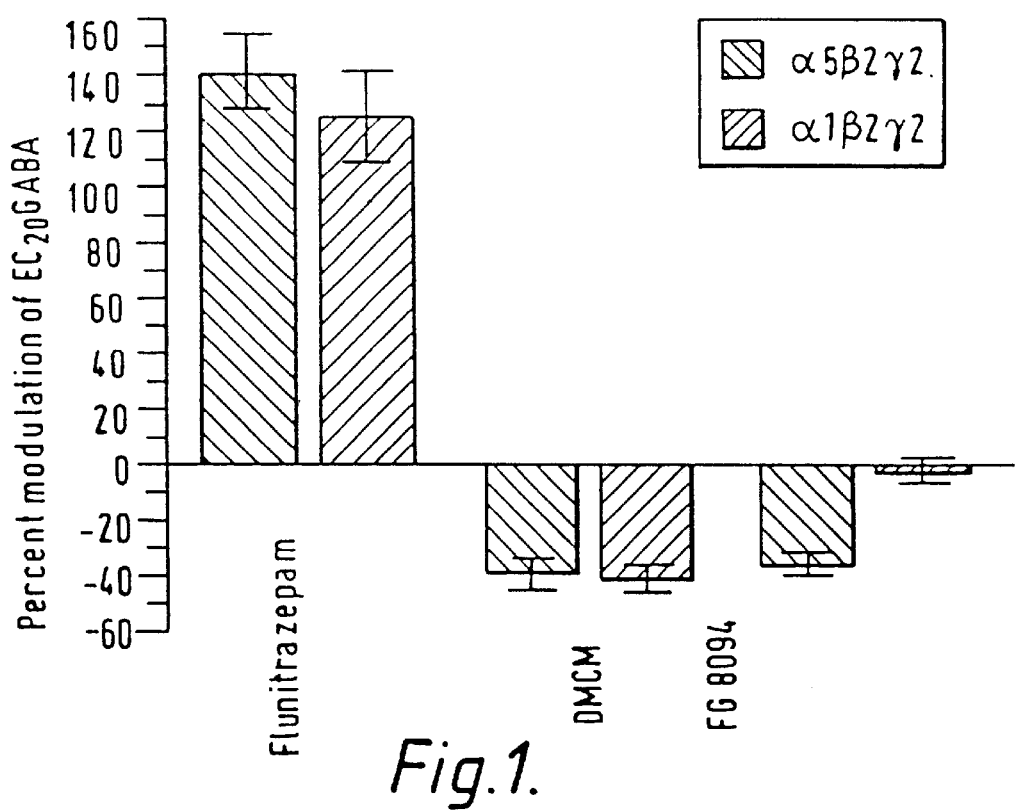

5 Claims, 3 Drawing Sheets n=8, route=i.p., *=p<0.05, Vehicle=0.5% CMC, pretreatment=30 min.

PREPARATION AND USE OF A SPECIFIC GABA-$_A\alpha_5$ RECEPTOR LIGAND FOR TREATMENT OF ALZHEIMER'S DISEASE This is a divisional of U.S. patent application Ser. No. 08/894,031, filed Jul. 24, 1997 which is a 371 of PCT/GB96/00377, filed Feb. 20, 1996 which claims the benefit of UK Patent Application No. 9503601.8, filed Feb. 23, 1995.

The present invention provides a method of treatment for enhancing cognition (for example in the treatment of dementing illnesses such as Alzheimer's disease), compositions useful in such a method and methods of manufacturing medicaments for said purpose.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness.

It has been reported by McNamara and Skelton in Psychobiology, 21:101–108, that the benzodiazepine receptor inverse agonist β-CCM enhanced spatial learning in the Morris watermaze. However, β-CCM and other conventional benzodiazepine receptor inverse agonists are proconvulsant which makes it clear that they cannot be used as cognition enhancing agents in humans.

However, we have now discovered that it is possible to obtain medicaments which have cognition enhancing effects, but which do not possess proconvulsant effects previously described with benzodiazapine receptor inverse agonists.

The benzodiazepine receptor site is in the $GABA_A$ receptor, a structure that is generally accepted to be pentameric, with an integral chloride ion channel being formed by the second transmembrane domain of each of the five subunits. A family of 14 $GABA_A$ receptor subunits have been identified in mammalian brain using modern molecule cloning techniques, namely the $\alpha_1, \alpha_2, \alpha_3, \alpha_4, \alpha_5, \alpha_6, \beta_1, \beta_2, \beta_3, \gamma_1, \gamma_2, \gamma_3, \delta$ and $\phi$ subunits. Selection of five subunits from a possible repetoir of 14 allows for a multiplicity of possible combinations but the number of subtypes which occur and the extent of $GABA_A$ receptor heterogeneity remains unknown. When referred to hereinafter as a $\alpha_1, \alpha_2, \alpha_3, \alpha_5$ or $\alpha_6$ receptor, reference is of course made to the $GABA_{A\alpha1}, GABA_{A\alpha2}, GABA_{A\alpha3}, GABA_{A\alpha5}$ and $GABA_{A\alpha6}$.

It has now been discovered that use of an $\alpha_5$ receptor inverse agonist which is relatively free of certain activity at $\alpha_1$ and/or $\alpha_2$ and/or $\alpha_3$ receptor binding sites can be used to provide a medicament which is useful for enhancing cognition but which is not proconvulsant.

Accordingly the present invention provides a method of enhancing cognition without producing convulsions which method comprises administering to the subject in need thereof a cognition enhancing amount of a compound which is an $\alpha_5$ receptor inverse agonist which is not a receptor agonist or receptor inverse agonist at $\alpha_1$ and/or $\alpha_2$ and/or $\alpha_3$ receptors said amount being sufficient to enhance cognition without producing convulsions.

The method will be applied to a mammal, most aptly to a human and preferably to a human suffering from a dementing illness such as Alzheimer's disease.

Thus the compound employed will bind as an inverse agonist to $\alpha_5$ receptors at concentrations at which no significant agonist or inverse agonist binding occurs to $\alpha_1$ receptors. More suitably the compound will bind as an inverse agonist to $\alpha_5$ receptors at concentrations at which no significant agonist or inverse agonist binding occurs to $\alpha_1$ and $\alpha_2$ receptors. And most suitably the compound will bind as an inverse agonist to $\alpha_5$ receptors at concentrations at which no significant agonist or inverse agonist binding occurs to $\alpha_1, \alpha_2,$ and $\alpha_3$ receptors.

The inverse agonist binding at $\alpha_5$ may be partial (ie the compound may be a partial agonist) but a full inverse agonist at $\alpha_5$ is preferred. Similarly the compound should not be a full or partial agonist or inverse agonist at the other receptors.

The compounds employed may have antagonist binding at $\alpha_1, \alpha_2, \alpha_3$ and at $\alpha_6$ if desired as such binding will not adversely effect the operation of the method of this invention. When relative binding to the various receptors is concerned it is only the inverse agonist or agonist binding that is considered.

In general such compounds will bind at least 10 fold better to $\alpha_5$ receptors than $\alpha_1$ receptors, that is the compound will be at least 10 fold selective for $\alpha_5$ containing receptors over $\alpha_1$ containing receptors.

Aptly the compound for use in the invention at least 10 fold selective for $\alpha_5$ containing receptors over $\alpha_1$ and $\alpha_2$ containing receptors, more aptly at least 10 fold selective for $\alpha_5$ containing receptors over $\alpha_1, \alpha_2$ and $\alpha_3$ containing receptors and most aptly at least 10 fold selective for $\alpha_5$ containing receptors over $\alpha_1, \alpha_2, \alpha_3$ and $\alpha_6$ containing receptors.

Favourably the compound for use in the invention at least 25 fold selective for $\alpha_5$ containing receptors over $\alpha_1$ containing receptors, for example 25 fold selective for $\alpha_5$ containing receptors over $\alpha_1$ and $\alpha_2$ containing receptors, more aptly at least 25 fold selective for $\alpha_5$ containing receptors over $\alpha_1, \alpha_2$ and $\alpha_3$ containing receptors and most aptly at least 25 fold selective for as containing receptors over $\alpha_1, \alpha_2, \alpha_3$ and $\alpha_6$ containing receptors.

Preferably the compound for use in the invention at least 50 fold selective for $\alpha_5$ containing receptors over $\alpha_1$ containing receptors, for example $\alpha_1$ and $\alpha_2$ containing receptors, more aptly at least 50 fold selective for $\alpha_5$ containing receptors over $\alpha_1, \alpha_2$ and $\alpha_3$ containing receptors and most aptly at least 50 fold selective for $\alpha_5$ containing receptors over $\alpha_1, \alpha_2, \alpha_3$ and $\alpha_6$ containing receptors.

With advantage, the compound for use in the invention will be at least 100 fold selective for $\alpha_5$ containing receptors over $\alpha_1$ receptors.

The favoured method of this invention has the additional advantage of being able to enhance cognition without inducing unwanted anxiogenic effects.

A favoured receptor for determining $\alpha_5$ binding is the $\alpha_5 \beta_3 \gamma_2$ receptor. A favoured receptor for determining the $\alpha1$ binding is the $\alpha_1 \beta_3 \gamma_2$ receptor. A favoured receptor for determining $\alpha_2$ binding is the $\alpha_2 \beta_3 \gamma_2$ receptor. A favoured receptor for determining $\alpha_3$ binding is the $\alpha_3 \beta_3 \gamma_2$ receptor. A favoured receptor for determining the $\alpha_6$ binding is the $\alpha_6 \beta_3 \gamma_2$ receptor.

Receptors are described in International Patent Application No WO 92/22652 and WO94/13799.

The compounds for use in the method of this invention may be identified by screening against the above identified receptors using techniques known in the art. Favoured techniques include those described in Goeders et al (see hereinafter).

The determination of whether the compounds are receptor agonists, receptor partial agonists or receptor inverse agonists can likewise be determined using techniques known in the art. Favoured techniques include those described in Wafford et al (see hereinafter).

Particularly suitable compounds for use in this invention will have a Ki value (nM) against the $\alpha_5 \beta_3 \gamma_2$ receptor of less than 5, more suitably less than 2 and most suitably less than 1, for example about 0.5.

Particularly suitable compounds for use in this invention will have a Ki value (nM) against the $\alpha_1 \beta_3 \gamma_2$ receptor of greater than 10, more suitably greater than 20, most suitably greater than 40, for example about 50.

Particularly suitable compounds for use in this invention will have a Ki value (nM) against the $\alpha_2 \beta_3 \gamma_2$ receptor of greater than 5, more suitably greater than 10, most suitably greater than 20, for example about 25.

Particularly suitable compounds for use in this invention will have a Ki value (nM) against the $\alpha_3 \beta_3 \gamma_2$ receptor of greater than 5, more suitably greater than 10, most suitably greater than 20, for example about 25.

Particularly suitable compounds for use in this invention will have a Ki value (nM) against the $\alpha_6 \beta_3 \gamma_2$ receptor of greater than 10, more suitably greater than 20, most suitably greater than 40, for example about 80.

In order to exhibit their activity without having to administer the compounds intravenously, the compounds for use in this invention are most preferably able to cross the blood brain barrier after oral administration.

A compound which possesses the desirable properties outlined above which illustrates the usefulness of possessing those properties is FG 8094.

The present invention also provides a pharmaceutical composition for use in the enhancement of cognition without producing convulsions which comprises a compound which is an $\alpha_5$ receptor inverse agonist which is not a receptor agonist or receptor inverse agonist at $\alpha_1$ and/or $\alpha_2$ and/or $\alpha_3$ receptors and a pharmaceutically acceptable carrier therefor.

The compositions are most aptly adapted for oral administration to humans although parenteral modes of administration are also envisaged, for example by intravenous, intramuscular or subcutaneous administration or topically or rectally.

For oral use of the cognition enhancer the selected compound may be administered for example in the form of a tablet or a pharmaceutically acceptable carriers or diluents, optionally with known adjuvants, such as alum, in a pharmaceutical composition according to standard pharmaceutical practice. The compounds can be administered orally, parenterally, including by intravenous, intramuscular, intraperitoneal or subcutaneous administration, or topically.

For oral use the cognition enhancer may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavouring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

For topical administration, the cognition enhancer may be formulated as, for example, a suspension, lotion, cream or ointment employing a pharmaceutically acceptable carrier such as, for examples water, mixtures of water and water-miscible solvents such as lower alkanols, vegetable oils, polyalkylene glycols and the like.

The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

When a cognition enhancer is used in a human subject, the daily dosage will normally be determined by the prescribing physician with the dosage generally varying according to the age, weight, and response of the individual patient, as well as the severity of the patient's symptoms. However, in most instances, an effective daily dosage will be in the range from about 0.005 mg/kg to about 100 mg/kg of body weight, and preferably, of from 0.05 mg/kg to about 50 m/kg, such as from about 0.5 mg/kg to about 20 mg/kg of body weight, administered in single or divided doses. In some cases, however. dosage outside these limits may be used.

Generally unit dose forms for oral administration will contain from 1 to 800 mgs, more usually 2.5 to 250 mgs, preferably 5 to 100 mgs, for example 10, 20 or 50 mgs.

A favoured cognition enhancer for use in this invention is 9H-imidazo[1,5-a]pyrrolo[2,1-C][1,4]benzodiazepine-1-carboxylic acid, 11, 12, 13, 13a-tetrahydro-7-methoxy-9-oxo-, ethyl ester, (S)-(9CI). The preparation of said compound is described in Canadian CA 1266671 A2 900313 (Division of Canadian Patent Application No 503 329).

This compound is sometimes known as FG 8094.

The compositions according to this invention may be prepared in any suitable manner, for example by conventional tabulating or capsule filling techniques of the like.

The present invention also provides the use of a cognition enhancer as hereinbefore indicated in the manufacture of a medicament for the enhancement of cognition without causing convulsions.

This invention also provides a method of identifying a compound capable of enhancing cognition without causing convulsions which method comprises employing $\alpha_5$ and $\alpha_1$ and/or $\alpha_2$ and/or $\alpha_3$ and/or $\alpha_6$ receptors to determine whether said compound is a ligand at $\alpha_5$ but not $\alpha_1$ and/or $\alpha_2$ and/or $\alpha_3$ and/or $\alpha_6$ receptors and determining whether the binding at $\alpha_5$ receptors is an inverse agonist and determining whether binding at the $\alpha_1$ and/or $\alpha_2$ and/or $\alpha_3$ and/or $\alpha_6$ receptors is agonist or inverse agonist.

This invention provides a method of detecting a compound capable of enhancing cognition without causing convulsions which method comprises employing $GABA_A$ binding receptor to determine that said compound is an $\alpha_5$ inverse agonist and is not an agonist or inverse agonist at $\alpha_1$ and/or $\alpha_2$ and/or $\alpha_3$.

This invention also provides a ligand previously unknown to be able to enhance cognition without causing convulsions which has been identified by a method of detection of this invention.

This invention further provides a pharmaceutical composition comprising a compound identified by the method of this invention.

The following references provide useful background information: Goeders N E and Kuhar M J (1985) Benzodiazepine binding in vivo with [$^3$H]Ro 15-1788. Life Sci 37:345–355.

McKernan R M. Quirk K, Prince R, Cox P A, Gillard N P Ragan C I and Whiting P J (1991) GABA$_A$ receptors immunopurified from rat brain with α-subunit specific antibodies have unique pharmacological properties. Neurone 7:667–676.

Quirk K, Gillard N P, Ragan C I, Whiting P J and McKernan R M (1994) Y-Aminobutyric acid Type A receptors in the rat brain can contain both Y2 and Y3 subunits but Y1 does not exist in combination with another Y-subunit. Mol Pharmacol 45:1061–1070.

Wafford K A, Whiting P J and Kemp J A (1993) Differences in affinity and efficacy of benzodiazepine receptor ligands on recombinant GABA$_A$ receptor subtypes. Mol. Pharmacol 43:240–244.

Whiting P W, Wafford K and McKernan R M (1996) GABA$_A$ receptors in the central nervous system. International Reviews in Neurobiology.

Wisden W, Herb A., Wieland H., Keinanen K, Luddens H and Seeberg PH (1991) Febs Lett 289, 227–230.

EXAMPLE 1

FG 8094 was suspended in 0.5% carboxymethylcellulose solution to provide an injectable solution.

EXAMPLE 2

The following examples illustrate pharmaceutical compositions according to the invention.

|  | Amount mg | |
| --- | --- | --- |
| Tablets containing 1–25 mg of FG 8094 | | |
| Compound of formula (I) | 5.0 | 25.0 |
| Microcrystalline cellulose | 20.0 | 20.0 |
| Modified food corn starch | 20.0 | 20.0 |
| Lactose | 54.5 | 34.5 |
| Magnesium Stearate | 0.5 | 0.5 |
| Tablets containing 26–100 mg of FG 8094 | | |
| Compound | 50.0 | 100.0 |
| Microcrystalline cellulose | 80.0 | 80.0 |
| Modified food corn starch | 80.0 | 80.0 |
| Lactose | 189.5 | 139.5 |
| Magnesium Stearate | 0.5 | 0.5 |

FG 8094, cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 3

Example FG 8094 (1.5 mg) was combined with hydroxy propylmethylcellulose (58.5mg) to form a small pellet. The pellets were implanted subcutaneously in rats. The resulting blood levels of FG 8094 were greater than 100 ng/ml for more than 6 hours.

General Methods
1. Radioligand binding studies.

Radioligand bindingstudies were carried out using membranes prepared from cells stably transfected with the following subunit combinations:-α1β3γ2, α2β3γ2, α3β3γ2, α5β3γ2, α6β3γ2. Incubations were carried out using 20–100 mg of membrane protein in a total volume of 0.5 ml in 10 mM Tris-HCl, 1 mM EDTA pH 7.4 for one hour at room temperature prior to termination through Whatman GF/C filters followed by 3×3 ml washes with 5 mM Tris-HCl pH 7.5 and scintillation counting. [$^3$H]Ro 15-1788 was used as a radioligand to label GABA$_A$ receptors with the exception of cells expressing α6β3γ2 where [$^3$H]Ro 15-4513 was used because this receptor type does not bind [$^3$H]Ro 15-1788 with high affinity. Non-specific binding was determined using 10 μM Ro 15-4513 and radioligands were used at concentrations equivalent to twice their Kd values for each subtype. Ki values were calculated according to the Cheng-Prussof equation.

2. In vivo [$^3$H]Ro 15-1788 binding in the mouse brain

The in vivo binding of [$^3$H]Ro 15-1788 to mouse brain was performed essentially as described by Goeders and Kuhar (1985). Male Swiss-Webster mice received a 0.9% NaCl solution containing 50 mCi/kg of [$^3$H]Ro 15-1788 (0.05 ml/10 g of body weight) via the tail vein. Animals were sacrificed by decapitation three minutes later, at which time peak amounts of [$^3$H]Ro 15-1788 were measurable in the brain (data not shown). Thirty minutes prior to sacrifice, FG 8094 (0.3, 1.0, 3.0 and 10.0 mg/kg) or diazepam (30.0 mg/kg to define non-specific binding) was given intraperitoneally in 0.5% carboxy methyl cellulose (CMC). Each mouse brain was then rapidly removed, homogenised in 5.0 ml of 50 mM Tris HCl, 5.0 mM EDTA, pH 7.4 at 40° C. using an ultra-turrax homogeniser for 10 s at setting 5. In a separate series of experiments different brain regions, selected for their preferential expression of particular GABA subtypes were also examined. Binding of [$^3$H]Ro 15-1788 to cerebellum is almost exclusively α1-like (Quirk et al, 1994), whereas binding to spinal cord is indicative of binding to receptors containing α2 or α3-subtypes, α1, α4 and α5 are rare or absent in this region (Wisden et al, 1992). Brains were rapidly dissected into forebrain and cerebellum and the spinal cord was also removed. Each forebrain was homogenised in 4.0 ml of buffer (approximately 14 ml/g wet weight of tissue), each cerebellum was homogenised in 1.0 ml of buffer (approximately 14 ml/g wet weight of tissue) and each spinal cord in 1.0 ml of buffer (approximately 20.0 mg/g wet weight of tissue). Volumes (3×200 ml) of homogenate were filtered rapidly through GF/B filters, washed with 2×5.0 ml volumes of ice-cold buffer and the residual radioactivity was counted by liquid scintillation spectroscopy.

3. Electrophysiological Studies—Functional effects of FG 8094

Binding studies on transfected cells containing α1β3γ2S, α2β3γ2S, and α5β3γ2S have identified compounds with α5 selectivity. These compounds were studied using electrophysiological techniques (Wafford et al, 1993) to determine their functional effects on α1β2γ2S, α2β2γ2S, α3β2γ2S, α5β2γ2S and α6β2γ2S GABA$_A$ receptors expressed in *Xenopus oocytes*. Oocyte nuclei were directly injected with 10.0–20.0 nl of the relevant cDNAs (6.0 ng/μl) engineered into the expression vector pCDM8. Following incubation for 24 h, oocytes were placed in a 50 ml bath and perfused with saline. By using the two electrode voltage-clamp recording method. GABA activated currents could be measured by bathing the cell in a solution containing GABA. Firstly a reproducible current response was established using a GABA concentration which gave approximately 20% of the maximal GABA response that could be elicited (EC$_{20}$). Coapplication of the test compound with this EC$_{20}$ concentration of GABA resulted in a modulation of the response via action at the BZ binding site. The response could be potentiated by a BZ receptor agonist or inhibited by BZ receptor inverse agonist 4. Seizure and Cognitive Studies.

Drugs

FG 8094 was synthesised by the Merck, Sharp and Dohme Neuroscience Research Centre's medicinal chemistry group and was suspended in 0.5% CMC. Vehicle or FG 8094 was administered IP 30 mins before the beginning of the first training trial.

Pro-convulsant Testing (i) Acute treatment

Sixty naive male Sprague Dawley rats (225–265 g) housed in groups of four with food and water freely available, served as subjects. The rats were assigned to one of six groups and given: Vehicle or 0.5, 1.0, 2.0, 4.0 mg/kg of FG 8904 or 10.0 mg/kg of the non-selective receptor inverse agonist, CGS 8216, a known pro-convulsant agent. Vehicle, FG 8094 or CGS 8216 was administered IP 30 min prior to an infusion of the convulsant, pentylenetetrazole (PTZ, 40 mg/ml). PTZ was infused into the tail vein of the rat at the rate of 1.0 ml/min. The latency to clonic and tonic seizure were recorded and the threshold to each was calculated using the equation: Threshold dose=infusion rate (ml/s)×PTZ (mg/ml)×(1000/rats weight)×latency (s).

(ii) Chronic Treatment

The rats used in this study received chronic treatment with FG 8094 during a MWM experiment. The rats were dosed IP once per day (Monday to Friday) and received a total of 24 doses. Following each drug administration rats were tested in a MWM and received the final dose of drug 48 h prior to convulsant testing. The subjects were assigned to one of four treatment groups (n=8) and given either Vehicle, 0.1, 0.3, or 1.0 mg/kg of FG 8094.

On the day of proconvulsant testing, the rats were restrained and pentylenetetrazole (PTZ, 40.0 mg/ml) was infused as described above. The latency (s) to both clonic and tonic (full extension) convulsion was recorded. Latency data were transformed to yield the dose of PTZ needed to reach the threshold of both clonic and tonic seizures.

Cognitive Studies

Animals

Male PVG hooded rats (Bantin & Kingman, Hull U.K.), weighting approximately 300 g, were housed in groups of four with free access to food and water. The animals were maintained on a 12/12 h light-dark cycle, with the lights on at 07:00 h.

Apparatus

The Morris watermaze consists of a white, fibre-glass circular pool, of diameter 2 m, filled with an opaque mixture of water and white dye (E308, Morton International) maintained at 26–28° C. The pool was located in the centre of a sound attenuated room, around the walls of which high contrast black and white patterned pictures were displayed as spatial 'extra maze' cues. 'North' was arbitrarily determined and the pool was divided up into four equal quadrants 'Northeast', 'Southeast', 'Southwest' and 'Northwest'. A hidden platform (13×13 cm) submerged 2 cm below the water surface was placed in the middle of the NE quadrant.

A closed-circuit video camera, fitted with a wide-angle lens, was mounted directly above the centre of the pool and connected to an image analyser which digitised the image. The digital information was relay to an Archimedes microcomputer running 'Watermaze' a software package supplied by Paul Fray LTD (Cambridge, UK). The software package provided the following measures: latency to reach the platform. length of path taken, average swimming speed, the time spent and the total distance travelled in the target quadrant.

Training

The rats were assigned to four treatment groups (n=8): Vehicle, 0.1, 0.3, 1.0 mg/kg FG 8094. During the acquisition phase of the experiment all the groups were given four trials per day. During this time the hidden platform was submerged in the NE quadrant of the watermaze. The rat was taken from the home cage and placed into the watermaze at one of four quasi-randomly determined locations ('North', 'East', 'South', or 'West') with its head facing, and almost touching, the pool wall. Trials began when the rat was released by the experimenter and ended when the rat climbed onto the platform and the mean escape latency was recorded. The maximum trial length was 60 s. If by that time the rat had not climbed on to the platform the trial ended automatically, the experimenter placed the rat on the platform and an escape latency of 60 s was recorded. The rat remained on the platform for 30 s and was then removed to a high-sided opaque plastic container for a further 30 s, (inter-trial interval, ITI). At the end of the ITI the rat was placed into the pool again, but at a different location and upon release the next trial began. This procedure was repeated until four trials had been completed.

Learning and Memory) tests

Probe trials

Normally, the escape latency declines over several days of training from 60 s to around 20 s. A 'probe trial' assess the rat's spatial memory for the location of the hidden platform. During this trial the platform was removed from the watermaze and the rat was allowed to search the pool for 60 s before it was removed from the pool. If the treatment improves the rat's memory for the location of the platform, it will spend longer searching the quadrant in which the platform had previously been hidden (NE) than a rat given vehicle treatment.

Cued Recall

Deficits in performance that might be due to drug-induced side-effects (such as blurred vision or motoric deficits resulting in an impaired ability to swim) were assessed using cued recall. In this procedure, the platform was also placed in the NE quadrant, but was raised 3 cm above the water level and thus visible to the rat. If the treatment has no effects on the mean escape latencies to the visible platform, then any group differences in mean escape latencies to an invisible platform can be attributed to an effect on cognitive process. The training schedule was identical to the training schedule used for acquisition training, and continued until the mean escape latencies did not significantly differ between groups.

Recall memory

Six days following the probe trial, during which time the rats were not expose to the watermaze or administered FG 8094, the rats were again tested with the platform submerged in the NE quadrant using the acquisition protocol.

Reversal learning

Reversal training was identical to the acquisition phase of the experiment with the exception that the platform was submerged in the middle of the SW quadrant.

Results

1. Selectivity of FG 8094 for $\alpha 5\beta 3\gamma 2$.

Competition curves at each of the cell lines show that FG 8094 is selective for receptors which contain the $\alpha 5$-subunit (see Table 1). FG 8094 was 1071 fold selective for $\alpha 5$-containing receptors over $\alpha 1$, 60 fold selective over $\alpha 2$, 53 fold selective over $\alpha 3$ and 184 fold selective over $\alpha 6$. This represents a novel pharmacological profile since most selective BZs, such as zolpidem or CL 218,872 have greater affinity for $\alpha 1$ than for $\alpha 5$-containing receptors (Pritchett and Seeberg, 1990). FG 8094 has the greatest preference for α5-containing receptors over α1-containing receptors than any other compound reported to date.

2. Occupancy of $GABA_A$ subtypes based on displacement of [$^3$H]Ro 15-1788 binding from whole brain by FG 8094 in vivo.

Three minutes after [$^3$H]Ro 15-1788 was administered intravenously into mice significant levels of radioactivity were present in the brain. It was estimated that greater than 95% of [$^3$H]Ro 15-1788 was associated with membranes as greater than 95% of the radioactivity was retained after filtration of the homogenates (data not shown). Diazepam (30.0 mg/kg) displaced 90% of the [$^3$H]Ro 15-1788 binding in the brain indicating that ligand present in the membranes was bound to $GABA_A$ receptors. When given intraperitoneally at doses of up to 3.0 mg/kg, FG 8094 did not significantly displace specific [$^3$H]Ro 15-1788 binding (data not shown). This implies that the number of any other $GABA_A$ receptor subtype occupied at these doses would have to be small and below the limit of detection in this assay. Since PG 8094 has highest affinity for α5-containing receptors (Table 1) and these represent less than 5% of the total $GABA_A$ receptor population, it is possible that doses ≦3.0 mg/kg of FG 8094 are occupying this subtype. At 10.0 mg/kg FG 8094 significantly displaced [$^3$H]Ro 15-1788 binding (p<0.05). Receptors containing al, α2 and α3 subunits form the three largest subtypes in the brain and account for approximately 90% of $GABA_A$ receptors (McKernan et al, 1991, Whiting et al, 1994). At this dose it is likely that FG 8094 is occupying predominantly α2 and α3-containing receptors (for which it has higher affinity than at α1-containing receptors). The receptors not displaced by FG 8094 at 10.0 mg/kg are most likely receptors containing an α1-subunit that comprise 40–50% of all $GABA_A$ receptors in the brain and for which FG 8094 has the lowest affinity.

The occupancy of α2, α3 and α1-containing receptors 30 min after administration of FG 8094 (1.0 mg/kg) was investigated more directly by assessing displacement of [$^3$H]Ro 15-1788 binding in brain region enriched in these subtypes. The cerebellum was used as an α1-selective tissue and the spinal cord as an α2/α3-selective tissue. The forebrain. which contains most subtypes of $GABA_A$ receptors was also included. Inhibition of in vivo binding of [$^3$H]Ro 15-1788 30 min after administration of FG 8094 (1.0 mg/kg) is shown in Table 2.

If it is assumed that the percentage inhibition of in vivo [$^3$H]Ro 15-1788 binding is a measure of receptor occupancy then the concentration at the receptor site in brain can be calculated according to Clarke's equation (occupancy=[drug]/[drug]+Ki). Substituting the occupancy determined at α1 and α2/3-containing receptors, the concentration of FG 8094 available at BZ binding sites in rat brain is 7.8 nM and 13.2 nM respectively. Occupancy at α5-containing receptors cannot be measured directly because of the low abundance of the receptor, but it can be calculated using the concentration of drug and binding affinity using Clarke's equation. This predicts 95–97% occupancy of α5-containing receptors 30 min after administration of FG 8094 (1 mg/kg).

3. Electrophysiological Studies—Functional effects of FG 8094

Figure 2:
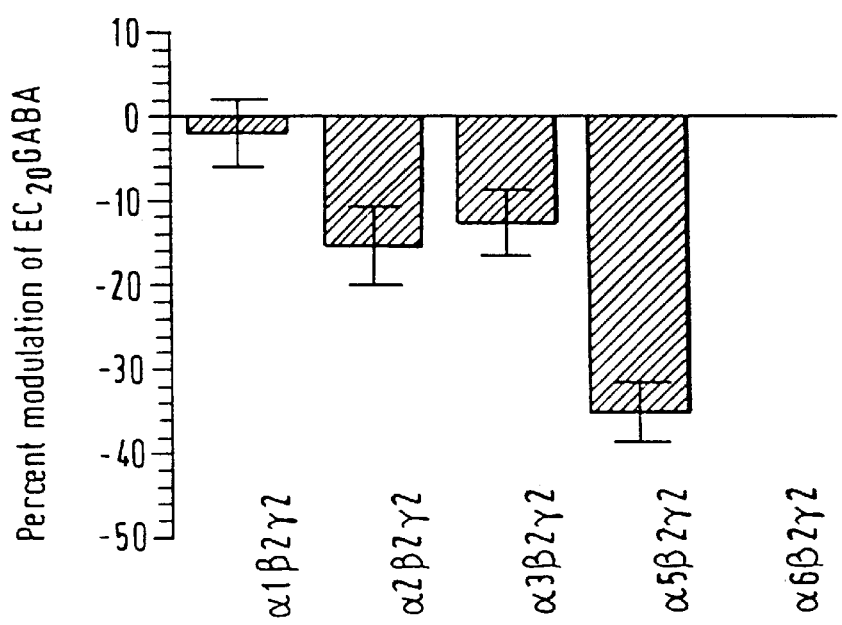

The modulatory effect on the GABA $EC_{20}$ is shown in FIG. 1 for FG 8094 at 1 μM, which would be near maximal for all the receptor subtypes studied, and two standard compounds flunitrazepam (1 μM, a full receptor agonist) and DMCM (1 μM, a full receptor inverse agonist) at concentrations which would be maximal in binding studies on α1β2γ2S. showing that FG 8094 is a full receptor inverse agonist on α5β2γ2. FIG. 2 compares the effects of FG 8094 on other α-subunit containing receptors, demonstrating that it has much lower efficacy at other α-subunit combinations. It has no intrinsic effect on α1β2γ2 suggesting it to be a low affinity antagonist, and it is a partial receptor inverse agonist on α2β2γ2 and α3β2γ2, receptors. A comparison of efficacy using a standard concentration of drug on α1β2γ2S demonstrated that FG 8094 is functionally selective for α5-containing receptors, exerting it's actions primarily via this subtype.

4. Seizure and Cognitive Studies (I) Acute Treatment—A one-way analysis of variance of the mean threshold doses for tonic and clonic revealed a main effect of tonic [F(5,49)=3.70; p=0.007], but not clonic [F(5,48)=2.01; p=0.09] seizures. Post hoc tests reveal that only CGS 8216 significantly lowered the threshold doses to tonic seizures, showing that it had a pro-convulsant effect.

(I) Chronic Treatment—An analysis of variance revealed no significant effect of treatment on the threshold dose of PTZ to either clonic [F(3,25)=0.23; p=0.87] or tonic [F(3, 25)=0.06; p=0.98] seizure. These results demonstrate that the chronic treatment protocol used in the study does not result in an increased sensitivity to the proconvulsant PTZ.

Acquisition trials

Figure 3A:
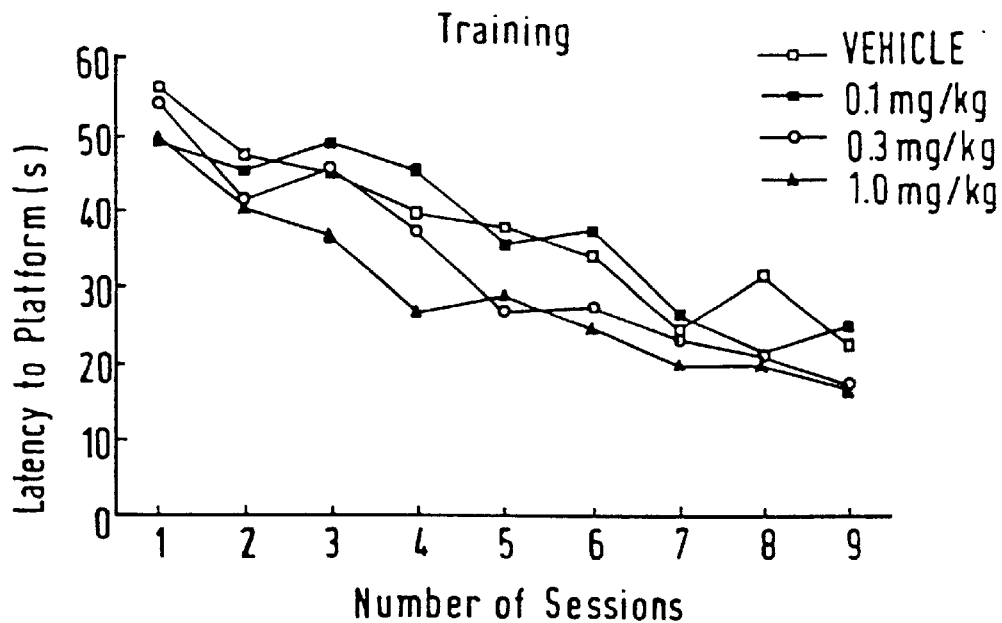

FIG. 3a illustrates the mean escape latencies during the nine day training period. An analysis of variance of the mean swimming speed during escape to the hidden platform revealed no significant effect of dose [F(3,28)=0.87], no significant effect of day [F(8,216)=1.44, p>0.1] and no dose by day interaction [F(24,216)=1.04, p>0.4]. An analysis of variance of the mean escape latencies with factors of treatment and day revealed a main effect of treatment [F(3,28)= 3.01, p<0.05], a significant effect of day [F(8,2 16)=34.67, p<0.00 1], but no dose by day interaction [F(24,216)=0.75, p>0.5]. Although the mean escape latencies of groups given 0.3 and 1.0 mg/kg of FG 8094 appear to be shorter than the vehicle control group or the 0.1 mg/kg group, the observation was not confirmed by Newman Keul post hoc tests.

Probe trials

Figure 3B:
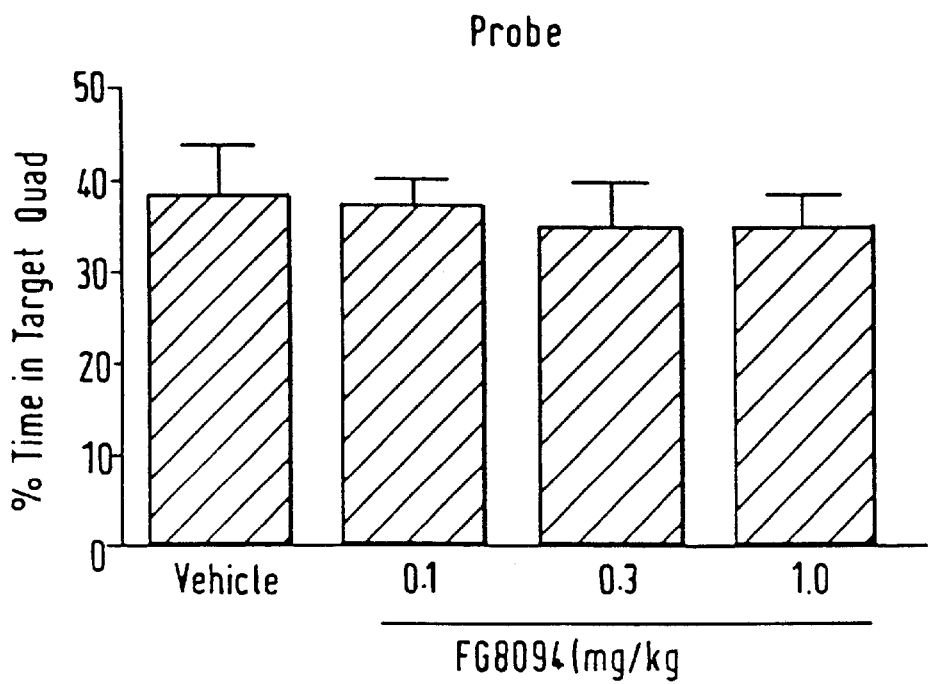

An analysis of variance of the percentage time spent swimming in the Northeast quadrant revealed no significant effect of dose [F(3,28)=0.18] (see FIG. 3b for details) which implies that the strength of the memory or the efficiency of acquisition did not differ between groups.

Cued Recall

Figure 3C:
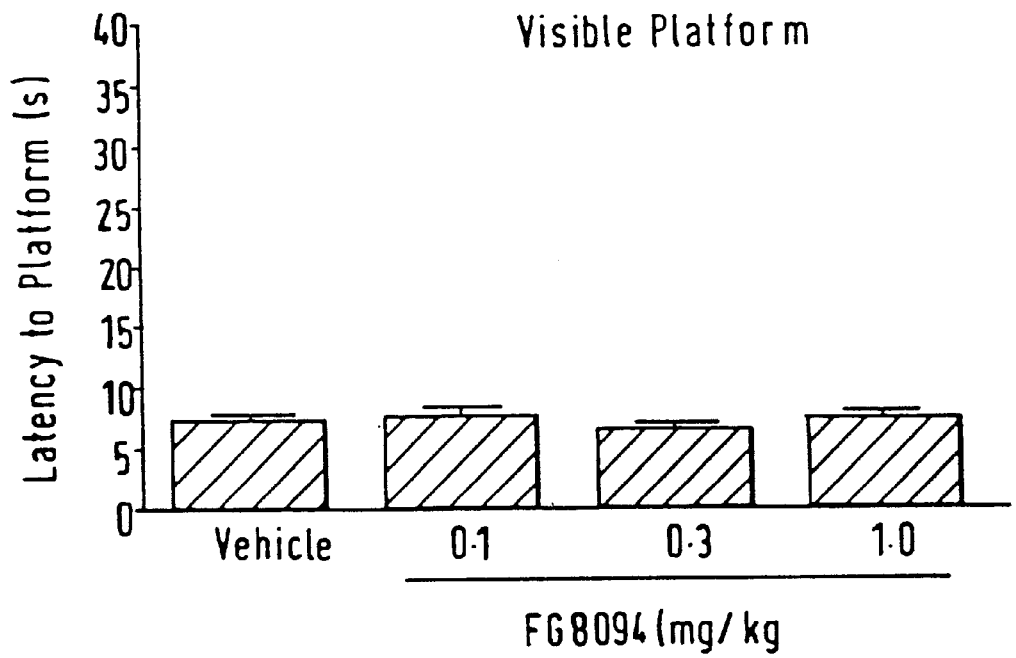

An analysis of variance of the mean escape latency to reach the visible platform showed no significant effect of dose [F(3,28)=0.54]. There was, however, a significant effect of dose on mean path length [F(3,28)=4.27, p<0.05]. Post hoc Newman-Keuls tests showed that the vehicle group traversed a significantly longer path than all the groups given FG 8094 (FIG. 3c)

Recall test

Figure 3D:
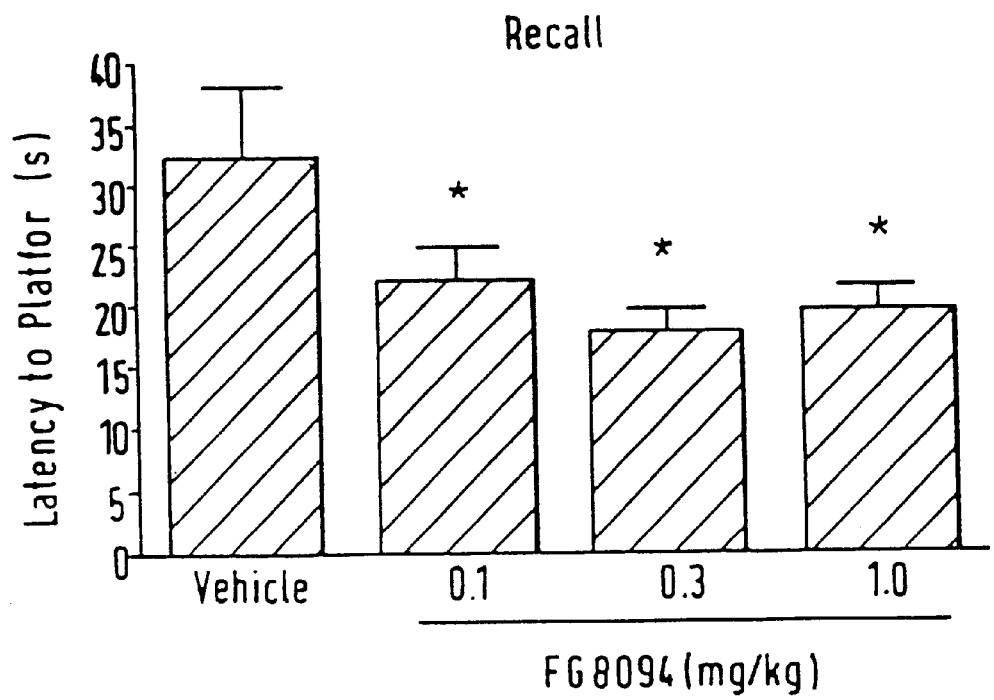

Analysis of variance of mean escape latency revealed a significant effect of dose [F(3,28)=3.53, p<0.05]. Post hoc Newman-Keuls test showed that the mean escape latency of the vehicle group was longer than any of the FG 8094 groups (p<0.05). These data suggest that the groups given FG 8094 retained the spatial information regarding the location of the hidden platform better than the vehicle control group (see FIG. 3d).

Reversal Learning

During reversal learning the platform was moved to the middle of the Southwest quadrant. An analysis of variance of the mean escape latencies revealed a significant effect of dose [F(3,28)=3.31, p <0.05], a significant effect of trial [F(3,84)=9.53, p<0.00 1], but no significant interaction [F(9,84)=1.66, p>0.1]. Post hoc Newman-Keuls test indicated that the mean escape latency of the vehicle group was significantly longer than all of the FG 8094 groups (p<0.05). On subsequent reversal learning days dose had no effect on the mean escape latencies. Thus, these data suggest FG 8094 enhanced the ability of the rats to learn a new spatial location for the hidden platform.

Discussion

Benzodiazepine receptor agonists, have anxiolytic and anti-convulsant effects in man and animals, but they also induce amnesia. Conversely, BZ receptor inverse agonists have anxiogenic and pro-convulsant effects, however they have cognition enhancing effects in animals. BZ receptor antagonists are without intrinsic effect, but they block the effects of both BZ receptor agonists and receptor inverse agonists. In contrast to full BZ receptor agonists, the present studies show that the selective $\alpha 5$ BZ receptor inverse agonist, FG 8094 is devoid of pro-convulsant effects, but has cognition enhancing effects in animals.

The results of the in vivo binding experiments showed that FG 8094 occupies virtually all $\alpha 5$-containing receptors at 1.0 mg/kg, whereas less than 35% and 15% of $\alpha 2/3$ and $\alpha 1$ receptors respectively are occupied. Therefore, at 1.0 mg/kg FG 8094 is selective for $\alpha 5$-containing receptors. At 10.0 mg/kg FG 8094 significantly occupies $\alpha 1$, $\alpha 2$ and $\alpha 3$ containing receptors and, as a consequence, FG 8094 is not selective for $\alpha 5$-containing receptors at doses above 1.0 mg/kg.

In electrophysiological experiments, FG 8094 was demonstrated to be a full receptor inverse agonist on the $\alpha 5\beta 2\gamma 2$ receptor subtype, a low partial receptor inverse agonist at receptor subtypes containing $\alpha 2$ or $\alpha 3$, and an antagonist on $\alpha 1,\beta 2\gamma 2$, the major subunit combination in the brain. These data suggests that the major in vivo effects of FG 8094 are exerted at the $\alpha 5$ containing subtype, which is predominantly located in the hippocampus.

In the MWM rats are trained to find a submerged platform in a pool of opaque water. It is assumed that the animals use the various visual cues placed around the walls of the room to guide their search strategy.

Such a process assumes flexible cognitive processing as the animal must first form a 'map' of the room (i.e. the spatial relationship between the stationary visual cues and the hidden platform) and then use the map to guide its path to the hidden platform. A well-trained rat, placed in to the pool at random locations, swims more or less directly to the hidden platform suggesting that it has detailed knowledge of the local area or a 'cognitive map', and it can plan a novel route to the hidden platform on each new trial.

In the present experiment inspection of FIG. 3a, which shows the mean latency (s) to find the hidden platform on successive days of training, suggests that the rats given 0.3 and 1.0 mg/kg consistently found the platform in less time than the vehicle or 0. 1 mg/kg groups, although this effect failed to reach statistical significance. During the probe trial, there was no difference in the amount of time the control and drug groups spent searching the quadrant in which the submerged platform had been placed during training trials, suggesting that there was no difference in the ability of the various groups to form and make use of a cognitive map. Similarly, there was no difference between the groups in their mean latencies (s) to find a visible platform indicating that FG 8094 was devoid of effects on motoric or sensory systems. However, on the first day of normal training, six days after the final visible-platform trial, the mean latency to find the hidden platform was significantly shorter in all the groups given FG 8094. These data imply that the spatial relationship between the location of the platform and the visual cues was retained and/or retrieved better by the rats given FG 8094 than those given vehicle. Moreover, when the hidden platform was move to a new location in the middle of the southwest quadrant, rats give 1.0 mg/kg of FG 8094 were quicker to learn about this new location than rats given vehicle.

In conclusion, FG 8094 is a selective $\alpha 5$ BZ receptor inverse agonist that is devoid of pro-convulsant effects. In MWM, a hippocampal dependent spatial memory test, FG 8094 significantly enhanced the ability of rats to retain spatial information, suggesting that it enhances cognitive processing.

TABLE 1

| Drug | $\alpha 1\beta 3\gamma 2$ | $\alpha 2\beta 3\gamma 2$ | $\alpha 3\beta 3\gamma 2$ | $\alpha 5\beta 3\gamma 2$ | $\alpha 6\beta 3\gamma 2$ |
| --- | --- | --- | --- | --- | --- |
| Flunitrazepam | 5.2 ± 0.2 | 2.5 ± 0.2 | 4.8 ± 1 | 2.11 ± 0.23 | >10.000 |
| Ro 15-4513 | 2.6 ± 0.11 | 2.6 ± 0.7 | 1.28 ± 0.06 | 0.24 ± 0.05 | 6.5 ± 0.6 |
| FG 8094 | 48.5 ± 6 | 27.4 ± 2.5 | 24.5 ± 2 | 0.45 ± 0.15 | 83.2 ± 4.5 |

Table 1. Ki values for benzodiazepine sites on stably transfected cells.

Inhibition curves were carried out using receptors labeled with [$^3$H]Ro 15-1788 at a concentration of twice the Kd. Ki values were calculated according to the Cheng-Prussof equation. Data shown are mean±SEM values for 3–6 determinations.

TABLE 2

|  | FG 8094 (mg/kg) | |
| --- | --- | --- |
| Tissue | 10 | 1 |
| Forebrain (all $\alpha$) | 53.3 ± 4.2 | 8.3 ± 3.2 |
| Cerebellum ($\alpha 1$) | 55 ± 6.9 | 13.8 ± 4.9 |
| Spinal cord ($\alpha 2/3$) | 74.2 ± 3.8 | 33.8 ± 7.4 |

Table 2.

Inhibition of in vivo [$^3$H]Ro 15-1788 binding in three brain regions after FG 8094.

Mice were injected intraperitoneally with FG 8094, 10 mg/kg or 1 mg/kg, 30 minutes prior to sacrifice and [$^3$H]Ro 15-1788 (0.1 mCi/g). Brain regions were dissected, homogenised and filtered as described in methods. Data are expressed as the percentage inhibition of binding relative to control (vehicle treated) animals and are the mean±SEM of 5 (10 mg/kg) or 10 (1 mg/kg) determinations.

Figure legend

FIG. 1 Effects of flunitrazepam (1 $\mu$M), DMCM (1 $\mu$M) and FG 8094 (1 $\mu$M) on the GABA EC$_{20}$ current response in oocytes expressing $\alpha 1\beta 2\gamma 2$ and $\alpha 5\beta 2\gamma 2$. Data is expressed as the mean±standard error of at least 4 separate oocytes.

FIG. 2 Effects of FG 8094 (1 $\mu$M) on the GABA EC$_{20}$ current response in oocytes expressing different $\alpha$-subunit containing receptors together with $\beta 2\gamma 2$. Data is expressed as the mean±standard error of at least 4 separate oocytes.

FIG. 3 The mean latency (s) to find a submerged platform in the northeast quadrant of the Morris watermaze on each day of training (a), the time spent searching the northeast quadrant expressed as a percentage of the total trial length (60s) (b), the mean latency (s) to find a visible platform in the northeast quadrant of the watermaze on the last day of visible-platform training (c) the mean latency (s) to reach a submerged platform in the northeast quadrant six days after the final training day (d) is shown for each treatment group following a 30 min pretreatment IP of vehicle or FG 8094 (doses as shown). '*' above a indicates that the mean for that group is significant different from the mean of the vehicle control group (post hoc Newman-Keuls tests, p<0.05 assumed).

Pelletised Administration

A subsequent watermaze experiment similar to that described above with the exception that a pellet of FG 8094 was implanted SC 2 hrs before the experiment began and all the training was conducted on one day, showed that FG 8094 again improved performace. In a second experiment the vehicle or FG pellets were implanted into rats exactly as described above. However, after the first four swim trials the animals were injected (IV) with [$^3$H]FG 8094 and three mins later the brains of the animals were rapidly removed. In vio binding showed that FG 8094 occurpied approximately 85% of α5 subtype containing GABA-A receptors in the brain. A third experiment identical to the second experiment with the exception that the animals were injected with [$^3$H]Ro 15-1788, showed that FG 8094 did not significantly occupy non-α5 subtype containing GABA-A receptors. This shows that (i) FG 8094 improved performance in the watermaze test of spatial memory (ii) that the dosing protocol used ensured that the brain levels of FG 8094 were sufficinet to occupy 85% of the α5 containing GABA-A receptors, without significantly occupying receptors containing other subtypes. These data demonstrate that the α5 receptor inverse agonist is beneficial in neurological disorders with an associated cognitive deficit and did not cause convulsions or sedation.

What is claimed is:

1. A method of identifying a compound for enhancing cognition, wherein said compound does not produce convulsions, said method comprising the steps of
presenting said compound to $GABA_A$ binding receptors; and
determining said compound is a $GABA_A$ selective $\alpha_5$ receptor inverse agonist; wherein said selective α5 receptor inverse agonist is
   i) a binding selective agonist which binds more strongly to $GABA_A$ receptors containing the $\alpha_5$ receptor subtype than receptors containing the $\alpha_1$, $\alpha_2$ or $\alpha_3$ subtypes; or
   ii) a functionally selective inverse agonist which is an inverse agonist at $GABA_A$ receptors containing the $\alpha_5$ receptor subtype while being substantially an antagonist at receptors containing the $\alpha_1$, $\alpha_2$ or $\alpha_3$ subtypes.

2. The method according to claim 1 wherein said $GABA_A$ selective $\alpha_5$ receptor inverse agonist binds at least 25-fold selectively to $\alpha_5$ receptors over $\alpha_1$ receptors.

3. The method according to claim 1 wherein said $GABA_A$ selective $\alpha_5$ receptor inverse agonist binds at least 50-fold selectively to $\alpha_5$ receptors over each of $\alpha_1$, $\alpha_2$, and $\alpha_3$-containing receptors.

4. The method according to claim 1 wherein said $GABA_A$ selective $\alpha_5$ receptor inverse agonist has a Ki (nM) value against the $\alpha_5\beta_3\gamma_2$ receptor of less than 2 and against the $\alpha_1\beta_3\gamma_2$ receptor of greater than 20.

5. The method according to claim 4 wherein said $GABA_A$ selective $\alpha_5$ receptor inverse agonist has a Ki (nM) value against the $\alpha_2\beta_3\gamma_2$ receptor of greater than 20.

* * * * *